(12) United States Patent
Erickson et al.

(10) Patent No.: US 9,024,012 B2
(45) Date of Patent: May 5, 2015

(54) METHODS TO TREAT MIXTURES OF GLYCOSIDES TO OBTAIN ONE OR MORE OF THESE GLYCOSIDES IN MORE PURE FORM

(75) Inventors: Aron Broman Erickson, Albertville, MN (US); John Joseph Hahn, Maple Grove, MN (US); Allan S. Myerson, Chicago, IL (US); Andrew Keith Ohmes, Jordan, MN (US); Troy Allen Rhonemus, Plymouth, MN (US); Kern M. Storo, Burnsville, MN (US); Christopher Austin Tyler, Minnetonka, MN (US)

(73) Assignee: Cargill, Incorporated, Wayzata, MN (US)

( * ) Notice: Subject to any disclaimer, the term of this patent is extended or adjusted under 35 U.S.C. 154(b) by 0 days.

(21) Appl. No.: 13/575,751

(22) PCT Filed: Jan. 27, 2011

(86) PCT No.: PCT/US2011/022741
§ 371 (c)(1),
(2), (4) Date: Jul. 27, 2012

(87) PCT Pub. No.: WO2011/094423
PCT Pub. Date: Aug. 4, 2011

(65) Prior Publication Data
US 2012/0289687 A1 Nov. 15, 2012

Related U.S. Application Data

(60) Provisional application No. 61/299,160, filed on Jan. 28, 2010.

(51) Int. Cl.
*C07H 1/08* (2006.01)
*C07H 15/24* (2006.01)
*A23L 1/236* (2006.01)
*A23L 2/60* (2006.01)

(52) U.S. Cl.
CPC *A23L 1/2366* (2013.01); *A23L 2/60* (2013.01)

(58) Field of Classification Search
CPC .......................................................... C07H 1/08
USPC .................................................. 536/128, 18.1
See application file for complete search history.

(56) References Cited

U.S. PATENT DOCUMENTS

| 5,962,678 | A | 10/1999 | Payzant et al. |
| 2006/0083838 | A1 | 4/2006 | Jackson et al. |
| 2007/0292582 | A1 | 12/2007 | Prakash et al. |
| 2008/0107775 | A1* | 5/2008 | Prakash et al. ............... 426/548 |

FOREIGN PATENT DOCUMENTS

| CN | 101220062 A | 7/2008 |
| WO | 2006045023 A2 | 4/2006 |
| WO | 2007149672 A2 | 12/2007 |
| WO | 2008091547 A2 | 7/2008 |

* cited by examiner

*Primary Examiner* — Elli Peselev

(57) ABSTRACT

The present invention provides methods to treat mixtures containing natural rebaudioside A (Reb A), rebaudioside B (Reb B), and rebaudioside D (Reb D), synthetic counterparts of these, and/or derivatives of the natural or synthetic embodiments obtain one or more of these glycosides in more pure form. In many embodiments, the invention can be used to process glycoside mixtures obtained at least in part from natural sources such as the *Stevia* plant. This allows, for instance, the recovery of a product including Reb A material in more pure form relative to Reb B material or Reb D material. As an alternative or in addition to recovery of the purified Reb A material, a product including Reb B material and/or Reb D material in more pure form relative to Reb A material can be obtained.

9 Claims, 7 Drawing Sheets

| 2θ | I/I0 (%) | 2θ | I/I0 (%) |
|---|---|---|---|
| 4.5 | 1.0 | 21.5 | 20.4 |
| 5.4 | 0.6 | 21.6 | 20.7 |
| 7.4 | 0.5 | 22.5 | 31.3 |
| 9.0 | 16.1 | 22.8 | 22.7 |
| 9.9 | 17.9 | 23.7 | 30.0 |
| 10.9 | 40.1 | 24.5 | 24.6 |
| 11.8 | 23.6 | 25.4 | 17.2 |
| 12.0 | 20.0 | 26.2 | 15.5 |
| 13.4 | 51.0 | 27.1 | 29.2 |
| 13.9 | 29.7 | 27.7 | 16.7 |
| 14.4 | 49.7 | 28.2 | 16.8 |
| 14.8 | 48.4 | 29.8 | 19.0 |
| 15.1 | 23.3 | 31.7 | 17.3 |
| 15.6 | 19.6 | 32.9 | 16.9 |
| 16.3 | 32.5 | 33.2 | 17.2 |
| 17.5 | 25.4 | 33.7 | 17.9 |
| 17.9 | 40.6 | 36.3 | 15.6 |
| 18.2 | 82.1 | 36.8 | 14.2 |
| 19.2 | 39.7 | 37.1 | 15.0 |
| 19.5 | 32.5 | 38.4 | 15.9 |
| 19.8 | 21.4 | 39.6 | 13.3 |
| 20.9 | 29.8 | | |

FIG. 4b

| 2θ | I/I0 (%) | 2θ | I/I0 (%) |
|---|---|---|---|
| 3.5 | 52.4 | 20.7 | 63.1 |
| 4.1 | 100.0 | 21.2 | 40.3 |
| 5.5 | 42.8 | 22.3 | 32.1 |
| 6.7 | 38.1 | 23.0 | 40.2 |
| 8.2 | 61.9 | 23.5 | 29.7 |
| 9.7 | 49.2 | 23.8 | 37.2 |
| 10.1 | 36.6 | 24.3 | 36.3 |
| 10.6 | 42.4 | 24.6 | 36.3 |
| 12.3 | 95.6 | 25.1 | 32.8 |
| 13.0 | 61.2 | 26.0 | 41.4 |
| 13.6 | 88.4 | 26.7 | 35.3 |
| 14.4 | 84.2 | 27.9 | 36.6 |
| 15.3 | 43.8 | 27.3 | 32.6 |
| 15.9 | 56.7 | 29.7 | 37.7 |
| 16.3 | 67.8 | 30.1 | 27.2 |
| 16.5 | 80.7 | 31.0 | 31.7 |
| 17.0 | 92.3 | 31.9 | 34.5 |
| 17.5 | 80.0 | 33.0 | 38.8 |
| 17.9 | 69.3 | 33.4 | 30.0 |
| 18.3 | 69.7 | 37.6 | 25.3 |
| 18.7 | 62.5 | 38.7 | 28.1 |
| 19.6 | 50.5 | 39.8 | 26.0 |
| 3.5 | 51.9 | 42.1 | 26.7 |

FIG. 5b

METHODS TO TREAT MIXTURES OF GLYCOSIDES TO OBTAIN ONE OR MORE OF THESE GLYCOSIDES IN MORE PURE FORM

CROSS REFERENCE TO RELATED APPLICATIONS

This application claims the benefit of PCT Patent Application Serial No. PCT/US11/022,741, filed Jan. 27, 2011, entitled METHODS TO TREAT MIXTURES OF GLYCOSIDES TO OBTAIN ONE OR MORE OF THESE GLYCOSIDES IN MORE PURE FORM, which application claims the benefit of U.S. Provisional Patent Application No. 61/299,160, filed Jan. 28, 2010, entitled METHODS FOR THE PURIFICATION OF REBAUDIOSIDE B AND REBAUDIOSIDE D FROM REBAUDIOSIDE A COMPOSITIONS, the disclosure of which is incorporated herein by reference.

FIELD OF THE INVENTION

The methods of the present invention relate to treatments that resolve mixtures including rebaudioside A material, rebaudioside B material, and rebaudioside D material into more pure form(s). For example, mixtures of rebaudioside A, B, and D can be resolved to provide the Reb A on the one hand, and/or the Reb B and/or D on the other hand, in more pure form. More specifically, the treatments use one or more crystallization strategies singly or in combination to purify such glycoside mixtures.

BACKGROUND

The species Stevia rebaudiana ("Stevia") has been the subject of considerable research and development efforts directed at the purification of certain naturally occurring sweet glycosides of Stevia that have potential as non-caloric sweeteners. Sweet glycosides (also referred to as steviol glycosides) that may be extracted from Stevia include the six rebaudiosides (i.e., rebaudioside A to F), stevioside (the predominant glycoside in extracts from wild type Stevia), dulcosides, and sterebins.

Rebaudioside A (Reb A) is a sweet tasting glycoside component of Stevia, having roughly 250-450 times the sweetness of sucrose. Rebaudioside A is desirable for use in non-caloric sweeteners because of its favorable sweetness profile, regulatory approvals, customer acceptance, and minimal bitter aftertaste. Rebaudioside B (Reb B) and D (Reb D) also are sweet tasting glycoside components of Stevia that are of interest for their sweetness characteristics.

The natural extracts of Stevia as well as some processed versions thereof as well as synthetic counterparts typically include mixtures of glycosides. It has been desirable to purify these mixtures to obtain one or more of these glycosides in more pure form. For instance, a mixture might include, among other ingredients, a combination of Reb A, Reb, B, and Reb D. It has been desirable in some instances to treat these mixtures to recover a product that includes Reb A in more pure form while reducing the content of Reb B and/or D in the product. In other instances, it may be desirable to treat these mixtures to recover a product that includes Reb B and/or Reb D in more pure form while reducing the content of Reb A in the product. In still other instances, these mixtures are processed to recover a combination of products. For instance, if a mixture is treated to recover a mixture portion that is more pure with respect to Reb A with reduced Reb B and Reb D, another portion of the treated mixture generally can be recovered that has more pure Reb B and/or D and less Reb A content Numerous methods have been reported for the purification of rebaudioside A from crude Stevia extracts containing rebaudioside A.

Japanese Publication No. 56121454 reports a method of separating stevioside and rebaudioside A at high purity and yield by crystallization. In the method a mixture of stevioside and rebaudioside A is extracted from the leaves and stalks of Stevia rebaudiana Bertoni by conventional process. The extract is dissolved in ≥70% aqueous solution of ethanol and rebaudioside A is selectively crystallized from the solution.

Japanese Patent 63173531 describes a method of extracting sweet glycosides from the Stevia rebaudiana plant. The first step of the process is to extract a liquid solution of sweet glycosides from the Stevia rebaudiana plant. Secondly, the liquid solution of sweet glycosides is passed through a non-polar porous resin and is eluted with a water-soluble organic solvent, preferably methanol. Thirdly, the eluted solution is concentrated and dried to give a powdery material. This procedure isolates a mixture of sweet glycosides, but does not isolate a single pure sweet glycoside such as rebaudioside A.

U.S. Patent Application Publication No. 2006/0083838 (Jackson et al.) reports a method of isolating and purifying rebaudioside A from commercially available Stevia rebaudiana starting material. The method comprises: (1) an ethanol (EtOH) formulation stage to formulate a selected EtOH solvent, (2) a first reflux stage using the Stevia starting material and optionally additional reflux stages using retentate isolated from a refluxed mixture or a stirred wash mixture, (3) optionally, one or more stirred wash stages, and (4) an ethanol purge and drying stage. In the reported method, an EtOH formulation stage is conducted in order to formulate a desired reflux solvent for use in the reflux step(s). Typically, the reflux solvent is a mixture of ethanol and water with about 5% to 15% by volume water. The reflux stage typically comprises providing a mixture of glycosides in the reflux solvent and refluxing the mixture for about 1 hour, cooling the mixture to improve the process yield, and filtering. The process further includes one or more energy-intensive refluxing steps that are typically conducted at a temperature of about 79° C. to 80° C. for about 1 hour. The stirred wash stage typically comprises providing a mixture of glycosides from a reflux stage and a solvent of pure ethanol, agitating the mixture at room temperature for about 15 minutes, and filtering. The method allegedly produces 100% pure, water-soluble rebaudioside A.

U.S. Pat. No. 5,962,678 (Payzant et al.) reports a method of extracting selected sweet glycosides from the Stevia rebaudiana plant. In the reported method, sweet glycosides are extracted from the Stevia plant and are processed to obtain individual components in a multi-step process. First, the Stevia plant is treated to extract an aqueous liquid solution containing mixed sweet glycosides. By using a series of ion exchange resins, the impure non-sweet glycosides are separated from the mixed sweet glycosides, which are dried. These dried mixed sweet glycosides, which still contain impurities, are then dissolved in a water-soluble organic solvent such as anhydrous methanol to form a solution. The solution is refluxed and is cooled to precipitate a first sweet glycoside component. This first sweet glycoside component, which is typically stevioside, can be recovered by filtration and may be further purified by the method described for the second component. The filtrate from the crystallization of the first precipitated sweet glycoside can be further treated to obtain a second sweet glycoside component by concentrating the filtrate by heating. Upon cooling the solution, a second sweet glycoside component precipitates which can be recovered. This second sweet glycoside component is typically rebaudioside A. It can be further purified by dissolving it in a water-soluble organic solvent such as methanol that may optionally contain a small amount of water. The solution is heated, refluxed, and finally cooled to precipitate the second sweet glycoside component at a higher purity. The precipitate can be recovered by filtration. This purification process can be repeated until a final crystallized solid of desired purity is obtained. The method reports Rebaudioside A purity levels of 90% or greater or 95% or greater.

U.S. Pat. No. 4,361,697 (Dobberstein et al.) reports a process for recovering diterpene glycosides from the *Stevia rebaudiana* plant. The process includes the steps of sequentially extracting plant material with a first solvent of intermediate polarity to extract plant substances which tend to interfere with a liquid chromatographic separation of the glycosides, and then with a second solvent of high polarity to extract glycosides, and chromatographically separating the extracted glycosides by introducing them onto a liquid chromatography column having a packing of an oxygen-containing organic stationary phase covalently bonded through a silicon atom to an inorganic support. The glycosides are eluted with a solvent of polarity that is higher than that of the first solvent but lower than that of the second solvent.

U.S. Pat. No. 4,892,938 (Giovanetto) reports a method for recovering steviosides from dried plant material of *Stevia rebaudiana Bertoni* by extraction and purification. An extract is obtained through treatment in water at a temperature from room temperature to about 65° C. with stirring and subsequent filtration and centrifugation. This extract is treated with calcium hydroxide, whereupon a precipitate is obtained by means of filtration or centrifugation. This precipitate is treated with a strongly acidic ion exchange resin and subsequently with a weakly basic ion exchange resin, filtered and dried.

U.S. Pat. No. 4,082,858 (DuBois) reports a method for the recovery of rebaudioside A from the leaves of *Stevia rebaudiana* plants. Final purification is achieved by liquid chromatography subsequently followed by an initial extraction with water and alkanol having from 1 to 3 carbon carbons, preferably methanol. It is also disclosed that water may be used as the initial solvent. Their preferred solvent at this stage is a liquid haloalkane having from 1 to 4 carbon atoms. The preferred second solvent is an alkanol having from 1 to 3 carbon atoms, while the preferred third solvent is an alkanol having from 1 to 4 carbon atoms and optionally minor amounts of water.

U.S. Patent Application No. 2006/0134292 (Abelyan et al.) reports a process for recovering sweet glycosides from *Stevia rebaudiana* plant material. The dried and powdered leaves are treated with water in the presence of a pectinase, cellulase, and alpha-amylase. The use of such enzymes is reported to considerably increase the extraction rate and facilitates the next stages of purification. The resulting extract is purified using treatment with calcium hydroxide and ultrafiltration. The permeate is passed through the column packed with bentonite and concentrated to syrup state under vacuum. The treatment with ethanol allows separating the practically pure rebaudioside A from the mixture. The rebaudioside A with high purity is obtained after washing the crystals with 88-95% of ethanol.

Other techniques include those reported, for example, in Japanese Publication Nos. 56121454; 56121455; 52062300; and 56121453 assigned to Ajinomoto Company, Inc, and in Chinese Publication No. 1243835 assigned to Hailin *Stevia Rebaudium* Sugar.

Due to their values as non-caloric sweeteners, improvements in the available methods for purifying glycosides such as Reb A, Reb B, and/or Reb D are desired. In particular, a method that allows for the separation of rebaudioside A from compositions containing rebaudioside B and/or rebaudioside D is highly desirable. This would allow recovery of a product that has more pure Reb A, a product that has more pure Reb B and/or D, or both kinds of products.

SUMMARY

The present invention provides methods to treat mixtures containing natural rebaudiosides A, B, and D, synthetic counterparts of these, and/or derivatives of the natural or synthetic embodiments to obtain one or more of these glycosides in more pure form. In many embodiments, the invention can be used to process glycoside mixtures obtained at least in part from natural sources such as the *Stevia* plant. This allows, for instance, the recovery of a product including Reb A in more pure form relative to Reb B or D. As an alternative or in addition to recovery of the purified Reb A, a product including Reb B and/or D in more pure form relative to Reb A can be obtained.

Principles of the present invention allow excellent purification of these glycosides to be achieved at high yield. Conventionally, high purity has been obtained at the expense of yield and vice versa. Providing methodologies that offer high levels of both yield and purification is a significant advantage, particularly at industrial scales.

The treatments of the present invention can be used in combination with other purification strategies. In such combinations, the methods of the present invention can be practiced before and/or after the other strategies are used. In some modes of practice, such combinations can be repeated one or more additional times.

In one aspect, the present invention relates to a method of treating a glycoside mixture comprising Reb A material and at least one of Reb B material or Reb D material to help recover at least one of the Reb A material, Reb B material, or Reb D material in more pure form, comprising the steps of:
 a) providing a slurry comprising glycosides including at least rebaudioside A material and at least one of Reb B material and D material, wherein the slurry includes a solid phase and a liquid phase;
 b) aging the slurry at one or more elevated temperatures independently greater than about 40° C., said aging occurring for a time period sufficient for the solid phase to become more pure with respect to at least one of the rebaudioside A material, B material and D material;
 c) filtering the heated mixture to separate the solid and liquid phases, wherein the mixture is at a temperature of at least 40° C. during at least a portion of the filtering; and
 d) recovering at least one glycoside in at least one of the solid and liquid phases.

In another aspect, the present invention relates to a method of treating a glycoside mixture comprising two or more of Reb A material, Reb B material or Reb D material to help recover at least one of the Reb A material, Reb B material or Reb D material in more pure form, comprising the steps of:
 a) providing a slurry comprising glycosides including at least Reb A material, Reb B material, and Reb D material, wherein the slurry includes a solid phase and a liquid phase; and
 b) aging the slurry at one or more elevated temperatures independently greater than about 85° C., said aging occurring for a time period and under conditions sufficient for at least one of (i) the solid phase to become more pure with respect to Reb A material relative to at least one of Reb B material and D material; and/or (ii) the liquid phase to become more pure with respect to at least one of Reb B material and D material relative to Reb A material.

In another aspect, the present invention relates to a method of treating a glycoside mixture comprising two or more of Reb A material, Reb B material or Reb D material to help recover at least one of Reb A material, Reb B material or Reb D material in more pure form, comprising the steps of:
  a) providing a slurry comprising glycosides including at least rebaudioside A material, B material and D material, wherein the slurry includes a solid phase and a liquid phase;
  b) aging the slurry at one or more elevated temperatures independently greater than about 40° C., said aging occurring for a time period sufficient for at least one of the solid phase and/or the liquid phase to become more pure with respect to at least one of the rebaudioside A material, B material and D material; and
  c) during at least a portion of the aging, agitating the heated slurry and causing successive portions of the heated slurry to contact a cooling surface.

In another aspect, the present invention relates to a method of treating a glycoside mixture comprising two or more of Reb A material, Reb B material or Reb D material to help recover Reb A material in more pure form, comprising the steps of:
  a) providing a first slurry comprising glycosides including at least rebaudioside A material, B material and D material, wherein the first slurry includes a solid phase and a liquid phase, said liquid phase comprising a first solvent;
  b) aging the first slurry, said aging occurring for a time period sufficient for the solid phase to become more pure with respect to Reb A material;
  c) incorporating at least a portion of the solid phase obtained in step (b) into a second slurry, wherein the second slurry includes a solid phase and a liquid phase, said liquid phase comprising a second solvent having a different composition than the first solvent; and
  d) aging the second slurry, said aging occurring for a time period sufficient for the solid phase to become more pure with respect to Reb A material.

In another aspect, the present invention relates to a method of treating a glycoside mixture comprising two or more of Reb A material, Reb B material or Reb D material to help recover at least one of Reb B material or Reb D material in more pure form, comprising the steps of:
  a) providing a first slurry comprising glycosides including at least rebaudioside A material, B material and D material, wherein the first slurry includes a solid phase and a liquid phase, said liquid phase comprising a first solvent;
  b) aging the first slurry, said aging occurring for a time period sufficient for the liquid phase to become more pure with respect to at least one of Reb B material or Reb D material;
  c) incorporating at least a portion of the liquid phase obtained in step (b) into a second slurry, wherein the second slurry includes a solid phase and a liquid phase, said liquid phase comprising a second solvent having a different composition than the first solvent; and
  d) aging the second slurry, said aging occurring for a time period sufficient for the liquid phase of the second slurry to become more pure with respect to at least one of Reb B material or Reb D material.

In another aspect, the present invention relates to a method of purifying an impure rebaudioside A composition, the method comprising the steps of:
  a) providing an impure rebaudioside A composition comprising rebaudioside A material and at least one impurity selected from the group consisting of rebaudioside B material and rebaudioside D material, wherein at least a portion of the rebaudioside A material is in a first crystalline form;
  b) converting at least a portion of the rebaudioside A composition from the first form into a second crystalline form; and
  c) converting at least a portion of the second crystalline form of the rebaudioside A composition to a third crystalline form said third crystalline form optionally being the same as the first crystalline form.

In another aspect, the present invention relates to a method of treating a glycoside mixture comprising Reb A material and at least one of stevioside material, Reb B material or Reb D material to help recover Reb A material in more pure form, comprising the steps of:
  a) providing a slurry comprising glycosides including at least stevioside, rebaudioside A material, B material and D material, wherein the slurry includes a solid phase and a liquid phase, and wherein the slurry includes less than about 60 weight percent Reb A material based on the total weight of glycosides in the slurry and wherein the liquid phase comprises ethanol; and
  b) aging the slurry at one or more elevated temperatures independently greater than about 85° C., said aging occurring for a time period and under conditions sufficient for the solid phase to become more pure with respect to Reb A material relative to at least one of stevioside, Reb B material and D material.

The purified glycoside compositions purified in accordance with the present invention are useful in sweetener compositions and in sweetened food and beverage compositions. Examples of food and beverage compositions include carbonated beverages, non-carbonated beverages (e.g., sports drinks and dry beverage mixes), ice cream, chewing gum, candy, juices, jams, jellies, peanut butter, yogurt, or cold cereal.

BRIEF DESCRIPTION OF THE FIGURES

FIG. 4b is a peak listing of a powder X-ray diffraction pattern for an ethanol crystal form of rebaudioside A useful in the present invention.
FIG. 5b is a peak listing of a powder X-ray diffraction pattern for a water crystal form of rebaudioside A useful in the present invention.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention. All patents, pending patent applications, published patent applications, and technical articles cited herein are incorporated herein by reference in their respective entireties for all purposes.

The present invention provides methods for treating glycoside mixtures containing rebaudiosides A, B, and D, derivatives of one or more of these, and/or synthetic counterparts of one or more of these natural and/or derivative foil is, to recover at least one of these glycosides in more pure form relative to the starting mixture. In addition to these glycosides, the mixtures optionally may include one or more other glycosides. Exemplary other glycosides include the steviol glycosides, derivatives of these, or synthetic counterparts. Mixtures of Reb A, B, and D obtained from natural sources also tend to include the other steviol glycosides.

The present invention is particularly useful for obtaining Reb A material in more pure form from these mixtures relative to at least Reb B material and D material. Thus, a purified composition obtained using principles of the present invention may have a larger percentage of Reb A material and a smaller percentage of Reb B material and/or D material than the starting mixture. Thus, in one aspect, the present invention provides methods for the removal of impurities such as rebaudioside B and rebaudioside D from impure rebaudioside A compositions.

Because the principles of the present invention can be used to separate Reb A material on the one hand from Reb B material and/or D material on the other hand, a purified composition obtained using principles of the present invention may have a larger percentage of Reb B material and/or D material and a smaller percentage of Reb A material than the starting mixture. Thus, in another aspect, the present invention provides methods for the removal of impurities such as Reb A from impure Reb B and/or D compositions.

Figure 1:
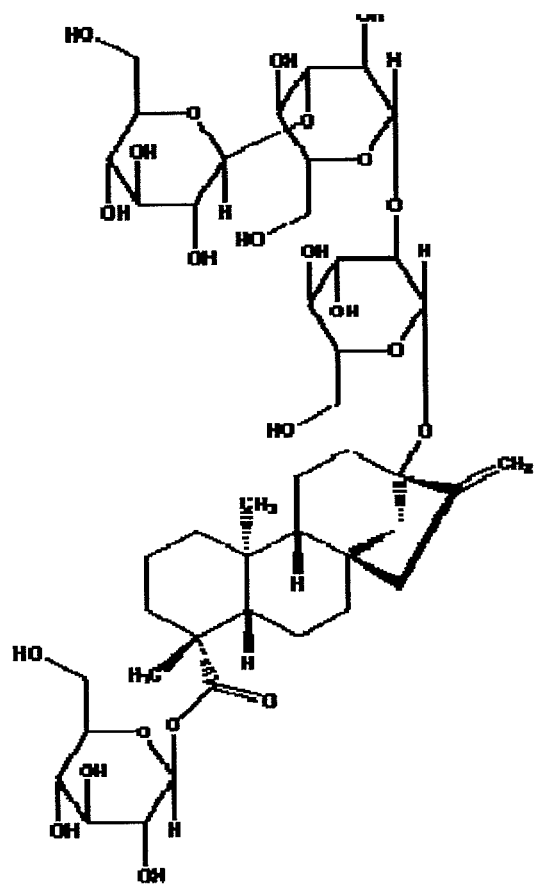
FIG. 1 is the chemical structure of rebaudioside A.

As used herein, the term "rebaudioside A" or "Reb A" refers to a compound having the chemical structure shown in FIG. 1. As used herein, the term "material" used with respect to a glycoside refers to that glycoside, derivative(s) of that glycoside, or synthetic counterpart(s) of the glycoside or its derivative(s). Thus, "Reb A material" refers to Reb A, Reb A derivative(s), and/or synthetic counterpart(s) of Reb A or Reb A derivative(s).

Figure 2:
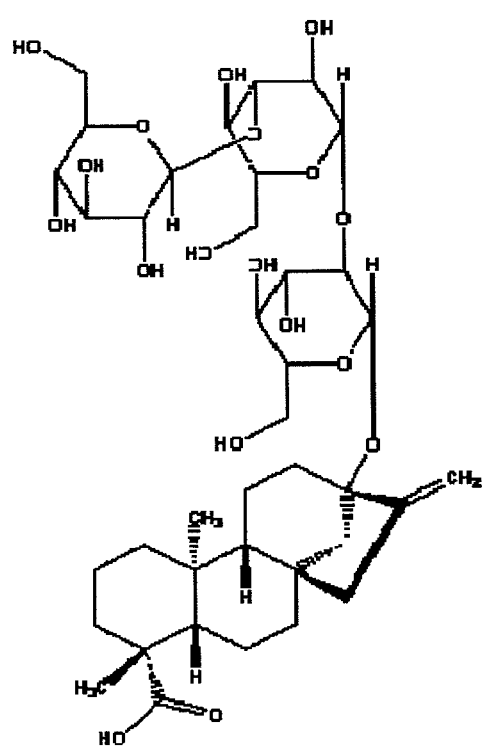
FIG. 2 is the chemical structure of rebaudioside B.

As used herein in the detailed description the term "rebaudioside B" or "Reb B" refers to a compound having the chemical structure shown in FIG. 2. As used herein, "Reb B material" refers to Reb B, Reb B derivative(s), and/or synthetic counterpart(s) of Reb B or Reb B derivative(s).

Figure 3:
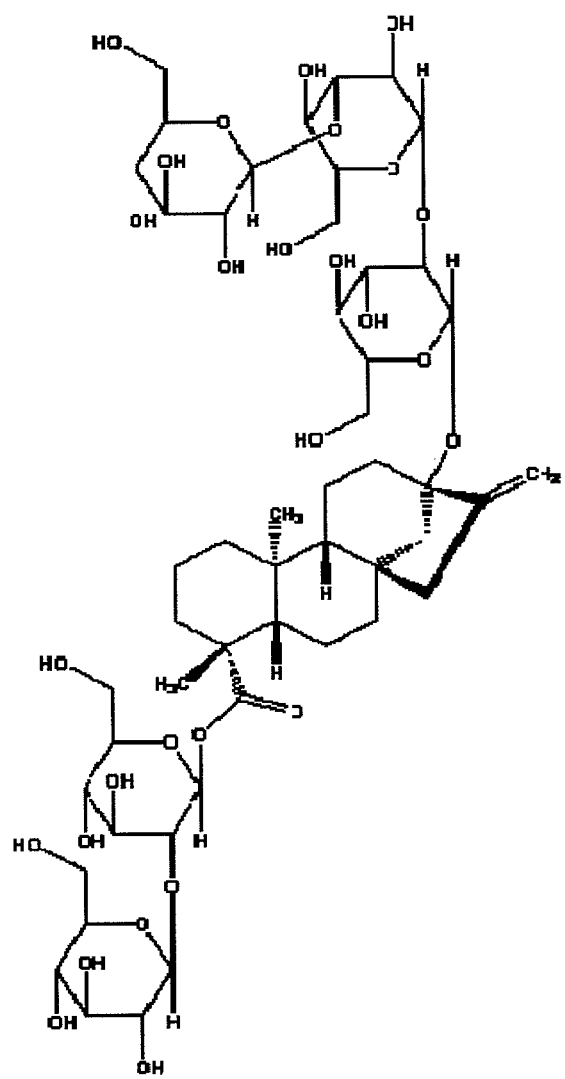
FIG. 3 is the chemical structure of rebaudioside D.

As used herein in the detailed description the term "rebaudioside D" or "Reb D" refers to a compound having the chemical structure shown in FIG. 3. As used herein, "Reb D material" refers to Reb D, Reb D derivative(s), and/or synthetic counterpart(s) of Reb D or Reb D derivative(s).

As used herein, a derivative of a glycoside molecule refers to a glycoside product that results from a modification of the glycoside by removing one or more moieties, adding one or more moieties, substituting one or more moieties for one or more other moieties, masking one or more moieties, adding or removing unsaturation, causing unsaturation to be at another location in the molecule, combinations of these, and the like; provided, however, that a derivative shall not include those molecules having modification(s) that change (e.g., increase or decrease) the number of sugar units in a carbohydrate portion that was, is, or becomes linked to the aglycone portion of the glycoside or that substitute one kind of sugar unit (e.g., a mannose unit in a representative circumstance) for another kind of sugar unit (e.g., a glucose unit in a representative circumstance). Derivatives do include modifications to the sugar unit(s), if any, that are present if the type and number of such sugar units does not change as a result of the modification.

For example, adding a sugar moiety to the Reb A carbohydrate portion that is linked to the aglycone via the natural ester linkage converts the Reb A to Reb D. The carbohydrate chain there is increased from one sugar unit to two sugar units. Such a modification yields Reb D, not a derivative of Reb A. Similarly, removing such sugar moiety from Reb A yields Reb B rather than a Reb A derivative where there is no longer a carbohydrate chain at such location.

A synthetic counterpart refers to a molecule that is substantially the same as a natural glycoside or a derivative of a natural glycoside except the counterpart is obtained via chemical synthesis rather than being obtained from a natural source. The stereochemistry of synthetic molecules may be the same or different than that of the natural counterpart. Where there are multiple chiral centers, some of these may be the same while others are different as between the synthetic and natural counterparts. The glycosides of the mixture can be provided in a variety of morphological and physical forms. For instance, the glycosides independently can be provided in crystalline, partially crystalline, and/or amorphous forms. Glycosides can be supplied in dry form or can be supplied as a constituent of a paste, slurry, or the like. In other instances, the glycosides can be at least partially dissolved and supplied in solutions, gels or the like.

In one mode of practice, at least a portion of the glycosides are crystalline and are provided in an alcohol crystalline form. Generally, this means that a glycoside has been crystallized in a liquid carrier including at least 80%, even at least 90%, even at least 95%, or even at least substantially 100% of one alcohol such as methanol, ethanol, ispropanol, n-butanol, combinations of these, and the like. Water is an exemplary co-solvent in such modes of practice. Aqueous alcohols desirably include at least about 80 weight percent, even at least about 90 weight percent, or even at least about 95 weight percent of alcohol(s). In some embodiments the ethanol that is used to prepare the slurry comprises 190 proof ethanol (i.e., 93-95 weight percent ethanol). Other grades of ethanol (e.g., 180 proof or 200 proof ethanol) may also be useful.

Ethanol crystalline forms are preferred, particularly in embodiments in which it is desired to obtain Reb A material in more pure form relative to Reb B material and Reb D material that might be in a starting mixture. Data has shown that the purity of the Reb A is higher when the treatment is applied to a glycoside mixture in which at least a portion of the Reb A is in an ethanol crystalline form. In other modes of practice, at least a portion of the glycosides are provided in a water crystalline form. Generally, this means that a glycoside has been crystallized in a liquid carrier including at least 80%, even at least 90%, even at least 95%, or even at least substantially 100% water.

Non-limiting examples of useful ethanol and water crystal forms are described in commonly assigned U.S. Provisional Application Ser. No. 61/168,072, filed Apr. 9, 2009, and entitled "SWEETENER COMPOSITION COMPRISING HIGH SOLUBILITY FORM OF REBAUDIOSIDE A AND METHOD OF MAKING" and its published counterpart PCT Pub. No. WO 2010/118218A1, each of these disclosures being independently incorporated herein by reference in its respective entirety.

Figure 4A:
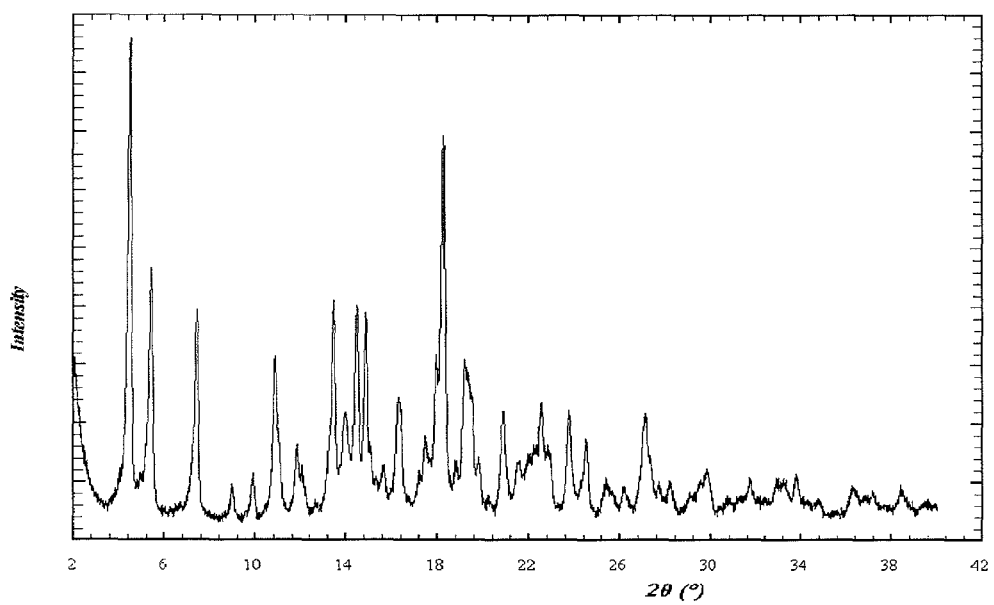
FIG. 4a is a powder X-ray diffraction pattern for an ethanol crystal form of rebaudioside A useful in the present invention.
Figure 5A:
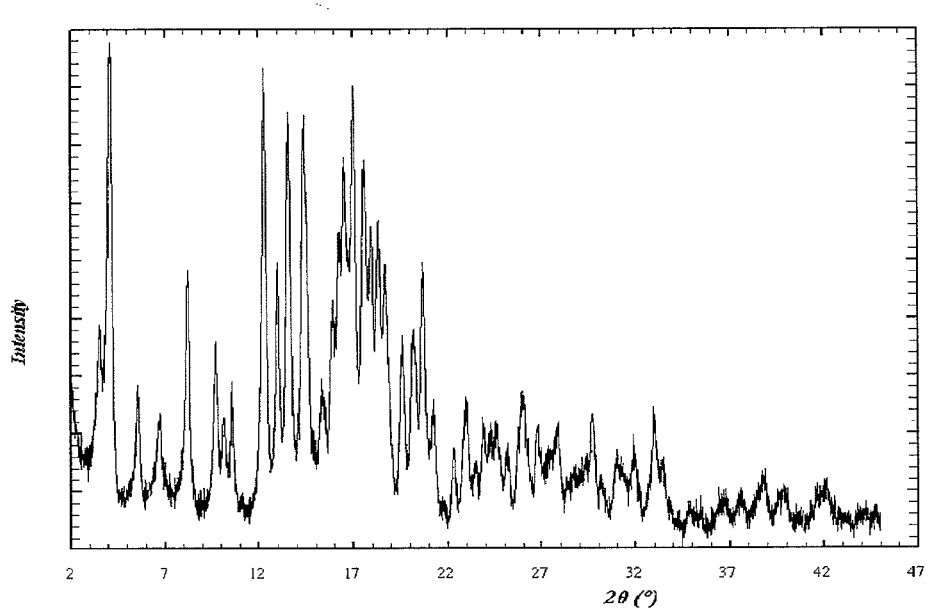
FIG. 5a is a powder X-ray diffraction pattern for a water crystal form of rebaudioside A useful in the present invention.

The crystalline form of a glycoside can differ depending upon the nature of the liquid carrier in which the glycoside was crystallized. For instance, the alcohol crystalline form of Reb A differs from the water crystalline form of Reb A. The ethanol crystal form may be characterized, for example, by having an X-ray diffraction pattern as shown in FIG. 4a. The water crystal form may be characterized, for example, by having an X-ray diffraction pattern as shown in FIG. 5a.

In some modes of practice, the principles of the present invention are applied to successive crystalline forms of the glycoside(s). Thus, the principles of the present invention may be applied to glycosides in a first stage of processing in which at least a portion of the glycosides are in a first crystalline form. By way of example, at least a portion of the glycosides are in an ethanol crystalline form in such first stage. In a subsequent processing stage, the principles of the present invention are then applied to the glycosides when at least a portion of the glycosides are in a second crystalline form. By way of example, at least a portion of the glycosides are in a water crystalline form in such subsequent stage. The first and/or second stages may be repeated as desired.

Those modes of practice in which the principles of the present invention are applied to successive crystalline forms of the glycoside(s) are referred to herein as form transition purification. This terminology indicates that the crystalline form of the glycoside(s) undergoes at least one crystalline form transition during the course of the treatment. Data has shown that the purity of a glycoside product such as Reb A is enhanced when incorporating form transition strategies into a purification treatment. Without wishing to be bound, it is believed that the enhancement arises because a crystalline glycoside dissolves in a liquid carrier and then re-crystallizes in the new crystalline form in the course of the transition. Hence, any impurities or other ingredients incorporated into a crystalline lattice are more easily released and/or separated as the crystal dissolves as compared to a mechanism in which the crystalline transition were to occur from one solid phase directly to another solid phase.

Exemplary modes of practice incorporating form transition purification are described further below including in the Examples.

According to the present invention, the glycoside mixture to be treated is incorporated into a slurry including at least one solid phase and at least one liquid phase. The solid phase(s) can be amorphous and/or crystalline. The slurry generally is obtained from ingredients that include at least the mixture to be treated and a suitable liquid carrier.

The amount of the glycoside mixture incorporated into the slurry can vary over a wide range. The concentration of the glycoside mixture in the slurry may be varied to affect the rate of purification. For instance, the removal of rebaudioside B and rebaudioside D from an impure rebaudioside A composition is impacted by this concentration. Generally speaking, as the concentration of the slurry increases (i.e., higher dissolved solids) the rate of separation of Reb A material on the one hand from Reb B material and Reb D material on the other hand tends to decrease. Having too much solids content also can make it more difficult to stir and filter the slurry during the course of the treatment. Yet, throughput, cost, and efficiency are reduced if the solids content is too low. Balancing such practical concerns, illustrative slurry embodiments include from about 5 weight percent to about 50 weight percent, preferably about 10 weight percent to about 40 weight percent, more preferably about 15 weight percent to about 30 weight percent of the glycosides based on the total weight of the slurry.

The slurry is heated to at least one elevated temperature above ambient temperature and is allowed to age at the elevated temperature(s). The aging occurs for a time period sufficient for at least one of (i) the crystalline phase to become more pure with respect to at least one of the glycosides (such as Reb A material) and/or (ii) the liquid phase to become more pure with respect to at least one of the other glycosides (such as at least one of Reb B material or D material). Longer aging tends to provide more purification. Thus, longer aging of the slurry increases the extent of removal of rebaudioside B material and rebaudioside D material from an impure rebaudioside A composition. The duration of aging is mainly subject to practical limits. For instance, after some duration, the amount of further purification that occurs slows down too much to be economically practical. Balancing such concerns in some embodiments, the slurry is aged for a period of time ranging from about 1 hour or greater, for example, from about 1 hour to about 24 hours. In a preferred aspect, the slurry is aged for a period of time ranging from about 3 to about 8 hours, or even about 4 to about 6 hours.

The liquid carrier desirably includes water, an alcohol, or a combination of these. Exemplary alcohols include methanol, ethanol, isopropanol, n-propanol, n-butanol, isobutanol, t-butanol, combinations of these, and the like. The alcohol(s) may be aqueous as discussed herein. In some embodiments the ethanol that is used to prepare the slurry comprises 190 proof ethanol (i.e., 93-95 weight percent ethanol). Other grades of ethanol (e.g., 180 proof or 200 proof ethanol) may also be useful.

The treatment may occur at a wide range of elevated temperatures. Desirably, boiling and reflux of the liquid carrier are avoided. Heat increases the rate and extent of separation of rebaudioside B material and rebaudioside D material from rebaudioside A material. Without wishing to be bound by theory, it is believed that one or more of the glycosides undergo conformational or other transformations that favor separation. In such embodiments, the slurry is heated at a temperature of at least about 40° C. to, preferably at least about 50° C., more preferably at least about 70° C., and even more preferably at least about 95° C. Heating desirably occurs up to a temperature of about 200° C., preferably 150° C., more preferably 120° C. In one mode of practice, heating at 100° C. is suitable.

When the mixture is well mixed, the bulk temperature generally is uniform throughout the mixture. In such well-mixed mixtures, the bulk temperature desirably is in such temperature ranges. When the mixture is not well-mixed such that a temperature gradient exists, then at least a portion, desirably at least about 5 volume percent, more desirably at least about 30 volume percent, more desirably at least about 50 volume percent of the mixture has temperature(s) in such temperature ranges.

The treatment may occur under a range of pressures. For instance, the treatment may occur under ambient pressure or elevated pressure(s) greater than ambient pressure. Elevated pressures allow the slurry to be heated at higher temperatures while staying below the boiling point of the liquid at the elevated pressure. Exemplary absolute pressures range from ambient pressure to about 30 atm, even about 1.1 atm to about 30 atm, preferably about 1.1 atm to about 15 atm, more preferably about 1.1 atm to about 10 atm, and even more preferably from about 1.1 atm to about 5 atm. In some modes of practice using liquid carriers comprising at least 90 weight percent ethanol in water, using a pressure of about 3 atm is suitable. Elevated pressures allow the use of higher temperatures in those embodiments in which it is desirable that the pressure is higher than the vapor pressure of the solvent at the desired temperature. This is desirable in that higher temperatures generally lead to better resolution among glycosides. For example, higher temperatures generally provide better resolution between Reb A material on one hand and Reb B material and D material on the other hand.

In some embodiments the slurry is agitated during treatment. Agitation generally increases the degree of purification. For example, agitation of a slurry comprising Reb A material, B material, and D material increases the rate and extent of separation of rebaudioside B material and rebaudioside D material from the rebaudioside A material. Typically agitation comprises, for example, mixing at high speed (e.g., 200 rpm) with an impeller in a baffled mixing vessel (e.g., a 5-liter baffled mixing vessel).

As the slurry is aged, the glycoside components are selectively partitioned between the solid and liquid phases. In the case of Reb A material, B material and D material, Reb A material tends to be more favored in the solid phase while Reb B material and D material are more favored in the liquid phase. This means more pure Reb A material is obtained in the solid phase, while more pure Reb B material and D material are in the liquid phase. The resultant solid phase also comprises crystalline content.

The two phases are easily separated by a variety of techniques, including filtration, to recover the desired purified material. If pure Reb A material is desired, the crystals can be filtered, washed, dried, further processed, or the like. If Reb B material and/or D material are desired, the liquid can be processed to recover the Reb B-material and D material as a dried product, a dispersion, a solution, or the like. A variety of drying techniques may be used including spray drying, oven drying, vacuum drying, combinations of these, and the like.

In preferred embodiments, the solid and liquid phases resulting from the treatment are separated by filtering. Desirably, the product mixture is at a temperature of at least about 50° C., preferably at least about 70° C. during at least a portion of the filtering. Hot filtration advantageously enhances separation of Reb B material and Reb D material from Reb A material in mixtures that include Reb A material, B material, and D material.

Without wishing to be bound, it is believed that separation is more favored at higher temperatures at least in part due to factors including conformational changes as well as solubility differences that are a function of temperature. At room temperature, the solubility of Reb B in a 94 weight percent ethanol solution saturated with Reb A is about 0.3 g per 100 g of solvent, and the solubility of Reb D is about 0.01 g per 100 g. At 100° C., concentrations of Reb D as high as 0.2 g/100 g are observed, and concentrations of Reb B as high as 0.5 g/100 g are observed. The solubility of Reb A in 94 wt % ethanol varies to a much smaller extent.

Aging the slurry at high temperatures thus increases the concentration of Reb B material and Reb D material in solution, and correspondingly decreases the Reb B material and Reb D material amounts in the solid phase. Hot filtration more easily allows the separation of Reb B material and Reb D material from Reb A material by separating the solids and liquid while maintaining the higher solubility of Reb B material and Reb D material. In contrast, cold filtering might risk precipitation of Reb B material and Reb D material such that the Reb B material and Reb D material concentrations in the liquid are closer to the room temperature solubilities. This can cause more Reb B material and D material to be in the solid phase, leading to less pure Reb A material in the solid phase. Thus, cold filtering can undermine purification gains obtained earlier in the treatment. If it is desired to cool prior to filtration, the slurry may be cooled only to the extent necessary. In one instance, cooling from 100° C. to 70° C. prior to filtration maintains the purification of the method while reducing the risks associated with filtration.

Although not wishing to be bound by theory, it is believed that purification occurs at least in part via solvent mediated crystallization due to the presence of both solid and liquid phases. In a slurry where solid and liquid phases are present, crystallization and dissolution occur simultaneously. This means that, at any one point in time, it might be true that only a portion of the glycoside(s) are in a crystal phase, while the remainder tends to be dissolved in the liquid phase. It is believed, however, that substantially all of the available glycoside(s) participate in dissolution and crystallization such that differing portions of the glycosides are continuously precipitating into one or more insoluble states while other portions are being converted into one or more soluble states. In short, while only some of the glycoside might be in one phase or the other at any one point in time, substantially all of the glycoside crystallizes and dissolves repeatedly over time. As successive portions are dissolved and crystallized, the partitioning between the phases, and hence the purity, becomes enhanced. The process is dynamic and can lead to changes in purity and shape over time.

In some embodiments, the dissolution and the crystallization occur generally at substantially equal rates such that there is very little if any net change in the macroscopic partition between the two phases. That is, molecules in the crystalline phase dissolve and molecules in the liquid phase can crystallize at substantially equal rates.

In some embodiments, particularly when the mixture is agitated during heat treatment, it is desirable if the heat treatment occurs in the presence of one or more cooling surfaces that are at a temperature that is less than the bulk temperature of the mixture being treated. Thus, as the mixture is agitated and thereby mixed during the course of the heat treatment, successive portions of the mixture will be in contact with the cooling surface(s). Even though mixing causes the bulk of the mixture to generally be at a uniform bulk temperature, heating the mixture in the presence of such cooling surface(s) has been found to enhance the purification. In contrast, merely subjecting the heated mixture to repeated cycles of heating and cooling has not been observed to provide the same purification enhancement.

Without wishing to be bound, a potential theory to explain the benefit of heating in the presence of a cooling surface can be suggested. The presence of both hot and cold surfaces in the mixture tends to favor crystallization near the cold surfaces but dissolution near the hot surfaces or in the hotter bulk mixture. By maintaining a cold surface in the mixture, crystallization and dissolution happen more frequently as crystals are convected from the cold zone to the hot zone, leading to higher purification at least for crystalline starting materials. The presence of both hot and cold surfaces also leads to larger particle sizes when using either crystalline or amorphous starting materials because smaller particles more rapidly dissolve due to a higher surface area to volume ratio. The higher purification may alternatively be due to the decreased fraction of small crystals in the mixture. It is also believed that using cold surfaces in the hot mixture may also increase the rate of purification for both amorphous and crystalline starting materials.

Generally, the cooling surface(s) are at one or more temperature(s) below about 40° C., preferably about 35° C. or less, even about 30° C. or less. Cooling surfaces can be provided in a variety of ways. In one embodiment, a cooling surface is provided by the surface of a coil that is immersed in the mixture and through which a cooling fluid flows. In such a mode of practice, the fluid might enter the immersed portion of the coil at an initial temperature, e.g., about 30° C. or less, even about 20° C. or less or even about 15° C. or less and exit the immersed portion of the coil at a moderately higher temperature due to heat transfer, such as about 5° C. or more warmer, even 10° C. or more warmer, or even 15° C. or more warmer. In another embodiment, the cooling surface is provided by an external heat exchanger, through which a portion of the slurry, drawn from and returning to the heating vessel, is circulated.

In a preferred embodiment of this aspect, the slurry can be heated under greater than ambient pressure as described above in order to more easily allow the treatment to occur at higher temperatures. It has been found that carrying out the treatment at higher temperatures under elevated pressure enhances the resolution between Reb A on the one hand and Reb B and D on the other hand.

Typically, the glycoside mixture that is used as a starting material in the method of the invention comprises a major amount of rebaudioside A material. A major amount means at least about 20 weight percent. Typically, the glycoside mixture may include from about 20 weight percent to about 96, preferably about 30 to about 96, more preferably about 40 to about 96 weight percent of Reb A material based on the total weight of glycosides. The total amount of both rebaudioside B material and rebaudioside D material in the mixture can vary. In many embodiments, the total amount of Reb B material and D material is up to about 6 weight percent based on the total weight of the glycosides. For example, in some embodiments the mixture comprises about 90 weight percent to about 96 weight percent rebaudioside A; about 1 weight percent to 4 weight percent rebaudioside B; and about 1 weight percent to about 4 weight percent rebaudioside D. A crystalline product obtained using the principles of the present invention may include at least about 80 weight percent, even at least about 90 weight percent, or even at least about 96 weight percent of Reb A.

It is quite advantageous that the present invention can be used to enhance the purity of Reb A material within glycoside mixtures containing about 60 weight percent or less, even 45 weight percent or less, or even 30 weight percent or less of Reb A material, particularly when the amount of stevioside material in such mixtures is at least about 10 weight percent of the total glycosides, or even at least about 20 weight percent of the total glycosides, or even greater than the amount of Reb A material in some embodiments. Reb A material in such compositions may be crystalline or amorphous, but often is at least partially amorphous. In many conventional processes when Reb A material is present in glycoside mixtures at such lower content levels, Reb A material is too soluble in solvents such as water or ethanol to be adequately crystallized and purified. Desirably, the liquid phase of the slurry(ies) used in such embodiments includes ethanol, desirably at least about 80 weight percent ethanol, or even at least about 90 weight percent ethanol, or even at least about 95 weight percent of ethanol based on the total weight of solvent incorporated into the slurry.

Without wishing to be bound, it is believed that such mixtures, particularly when obtained from natural sources, tend to include relatively greater amounts of stevioside material. The stevioside material tends to solubilize the Reb A material. The solvent mediated crystallization treatment of the invention, optionally in combination with form transition crystallization, is able to selectively partition Reb A material into a crystalline phase notwithstanding the solubilizing effects of stevioside material that otherwise would be expected to be a technical obstacle based on conventional experiences. Without wishing to be bound by theory, it is believed that elevated temperatures, particularly at 85° C. or higher, preferably 90° C. or higher, more preferably 100° C. or higher induce conformational changes in the steviol glycosides that promote crystallization of Reb A material even in such an unfavorable context.

It is also quite advantageous that the present invention can be used to boost the purity or Reb A material that is already highly pure. For instance, some conventional processes might be able to produce crystals that include about 90 weight percent to about 95 weight percent Reb A material. While such crystals are highly pure with respect to Reb A material pursuant to many applicable standards, there are other standards in which even more pure Reb A material is desired. The present invention can be applied to such crystals to boost the Reb A purity to as much as 96 weight percent, even 96 weight percent to 99 weight percent.

In one preferred embodiment of the method of the invention, a 30 weight percent slurry of impure rebaudioside A in 190 proof ethanol is heated to 70° C. and is held for about one hour with agitation. Following this, a retentate product including rebaudioside A crystals is recovered by filtration, and the retentate is washed with 190 proof ethanol (e.g., about 2 cake weights of solvent). The method results in the removal of about 30% rebaudioside B and about 50% rebaudioside D from the impure rebaudioside A composition. The yield of rebaudioside A is typically about 95 weight percent.

In another preferred embodiment of the method of the invention, a 30 weight percent slurry of impure rebaudioside A in 190 proof ethanol is heated to 70° C. and is held for about 24 hours with agitation. Following this, a retentate product including the rebaudioside A crystals is recovered by filtration and the retentate is washed with 190 proof ethanol (e.g., about 2 cake weights of solvent). The method results in the removal of about 50% rebaudioside B and about 50% rebaudioside D from the impure rebaudioside A composition. The yield of rebaudioside A is typically about 95 weight percent.

A representative purified rebaudioside A composition typically comprise about 97 weight percent or greater rebaudioside A material; about 2 weight percent or less rebaudioside B material; and about 2 weight percent or less rebaudioside D material. Other components that may be included in the purified rebaudioside A composition include, for example, stevioside material, rebaudioside C material, and rebaudioside F material.

Particularly preferred aspects of the present invention involve separating (also referred to as resolving) Reb A material on the one hand from Reb B material and/or D material on the other hand. In one such aspect, the present invention provides a method of purifying an impure rebaudioside A composition using effects that are believed to occur at least in part to solvent mediated crystallization. The impure rebaudioside A composition comprises at least one impurity selected from rebaudioside B material and rebaudioside D material. Desirably, at least the Reb A material is in an ethanol crystalline form.

In other embodiments, the Reb A material may be in other crystal forms and/or may be amorphous. The method comprises the steps of: (a) providing an impure rebaudioside A composition comprising rebaudioside A material and at least one impurity selected from rebaudioside B material and rebaudioside D material; (b) preparing a slurry of the impure rebaudioside A composition in a suitable liquid carrier such as ethanol; (c) aging the slurry for a period of time of about 1 hour or greater; (d) optionally, heating the slurry during at least a portion of the aging such as to a temperature of about 45° C. to about 100° C.; (e) optionally, agitating the slurry during at least a portion of the aging; and (f) after the aging step, filtering the slurry to collect the crystals (retentate) including the purified Reb A material, and washing the retentate to provide a purified rebaudioside A composition. In the purified rebaudioside A composition at least a portion of at least one of the impurities has been reduced as compared to the impure rebaudioside A composition.

In some aspects, the invention provides a method of purifying glycoside mixtures, such as an impure rebaudioside A composition, that incorporates form transition purification. In such embodiments, a glycoside mixture is provided wherein at least one glycoside is in a first crystalline form. For example, an impure rebaudioside A composition may be provided that comprises rebaudioside A material and at least one impurity selected from the group consisting of rebaudioside B material and rebaudioside D material. At least the Reb A material is in a first crystalline form such as an ethanol crystalline form. The ethanol crystalline form can be aged in a slurry as described above to enhance purity of the crystals with respect to Reb A material. The mixture is then treated to convert the glycoside into a second crystalline form. For example this may involve converting the rebaudioside A material from an ethanol crystalline form into a water crystalline form. The water crystalline form can be aged in a slurry as described above to enhance purity of the crystals with respect to Reb A material. Then, the water crystalline form of the rebaudioside A material can be converted from the water crystalline form to an ethanol crystalline form. Again, this form can be aged in a slurry as described above to enhance purity. This series of conversions helps to provide a purified rebaudioside A composition having a reduced amount of at least one impurity selected from rebaudioside B material and rebaudioside D material.

In some embodiments, the step of converting the ethanol crystal form to the water crystal form comprises: (a) combining the rebaudioside A composition with water to form a water-based slurry; and (b) allowing the water-based slurry to stand for a period of time sufficient to convert the ethanol crystalline form to a water crystalline form. The water crystalline form may be described as a four-hydrate polymorph of rebaudioside A. In some embodiments, the step of converting the water crystal form to the ethanol crystal form comprises: (a) combining the rebaudioside A composition with ethanol to form an ethanol-based slurry; and (b) allowing the ethanol-based slurry to stand for a period of time sufficient to convert the water crystal form to an ethanol crystalline form. The solids content, solvent characters, agitation, temperatures, pressures can be selected as described above with respect to the solvent mediated crystallization techniques. However, the ethanol used to convert the water form to the ethanol form typically comprises greater than about 93 weight percent ethanol although other concentrations may also be used.

The form transition purification results in the removal of rebaudioside B material, rebaudioside D material, or both from the impure rebaudioside A composition (i.e., the starting material). In some embodiments, the form transition results in the removal of up to about 50% of the rebaudioside B and up to about 95% of the rebaudioside D that was present in the impure rebaudioside A composition.

The principles of the present invention can be used in combination with other purification strategies. For example, PCT Pub. No. WO 2008/091547A2 describes a method of purifying glycosides such as Reb A using solvent/antisolvent/solvent techniques. The present invention can be used prior to and/or after such solvent/antisolvent/solvent techniques to obtain purified Reb A even more effectively and/or efficiently. PCT Pub. No. WO 2008/091547A2 is incorporated herein by reference in its entirety for all purposes.

The invention will now be described with reference to the following non-limiting examples.

EXAMPLE 1

Each of three samples of glycoside material containing the 90%, 95%, 92% Reb A %, respectively, and 2.9%, 0.1%, 1.0% Reb D, respectively, and 0.07%, 3.0%, 1.4% Reb B, respectively, in the ethanol crystalline forms was mixed with water to form a slurry of 13% solids in water. The slurry was agitated overnight at room temperature with a magnetic stir bar and stir plate, with sufficient agitation to keep all solid material suspended. After aging overnight, the material was filtered. The material contained 93%, 95%, and 95% Reb A, respectively; 2.4%, 0%, and 0.6% Reb D, respectively; and 0.5%, 3.9%, and 2.5% Reb B, respectively. The material recovered in the solid phase from each treatment was 88%, 98%, and 98%, respectively, of the total material fed to the process. The filtrate was dried in a vacuum oven, and contained 73%, 79%, 72% Reb A, respectively; 9.6%, 1.8%, 8.4% Reb D, respectively; and 0.4%, 3.7%, 0.5% Reb B, respectively.

EXAMPLE 2

Each of the three materials produced in Example 1 was slurried in pure ethanol in a slurry of 3.3%, 8.8%, 6.0% solids, respectively, and agitated overnight at room temperature. After the secondary aging, the material was again filtered, washed with 200-proof ethanol, and dried. Each filtered product contained 99%, 98%, 98% Reb A, respectively, 1.1%, 0.0%, 0.1% Reb D, respectively, and 0.1%, 1.3%, 1.0% Reb B, respectively. The overall yield of material in the solid phase, including the step in Example 1, was 64%, 83%, and 73%, respectively. The filtrate was dried in a vacuum oven, and contained 86%, 49%, 74% Reb A, respectively; 3.0%, 0.36%, 2.6% Reb D, respectively; and 1.6%, 19%, 11% Reb B, respectively.

EXAMPLE 3

Each of the three materials produced in Example 1 was slurried in 190-proof ethanol in a slurry of 6.9%, 4.9%, 7.2% solids, respectively, and agitated overnight at room temperature. After the secondary aging, the material was again filtered, washed with 190-proof ethanol, and dried. Each product contained 99%, 99%, 99% Reb A, respectively, 0.0%, 0.3%, 0.3% Reb D, respectively, and 1.0%, 0.1%, 0.6% Reb B, respectively. The overall yield of material recovered in the solid phase, including the processing in Example 1, was 68%, 45%, 71%, respectively. The filtrate was dried in a vacuum oven, and contained 74%, 81%, 73% Reb A, respectively; 10%, 2.3%, 9.7% Reb D, respectively; and 0.5%, 3.5%, 0.5% Reb B, respectively.

EXAMPLE 4

Each of three samples of glycoside material containing the 90%, 95%, 92% Reb A %, respectively, and 2.9%, 0.1%, 1.0% Reb D, respectively, and 0.07%, 3.0%, 1.4% Reb B, respectively, in the ethanol crystalline forms were processed as in Example 1. The collected solid material after processing contained 97%, 95%, 95% Reb A, respectively; 1.1%, 0%, 0.65% Reb D, respectively; and 0.9%, 3.9%, 2.9% Reb B, respectively. Each of the three collected solid materials was slurried in pure methanol at 5.1%, 6.0%, 5.3% solids, respectively, and agitated overnight at room temperature. After the secondary aging, the material was again filtered, washed with pure methanol, and dried. The product contained 99%, 99%, 99% Reb A, respectively, 0.2%, 0.0%, 0.2% Reb D, respectively, and 0.2%, 1.3%, 0.7% Reb B, respectively. The overall yield of material recovered in the solid phase, including the first step processing in water, was 41%, 64%, 58%. The filtrate was collected and dried in a vacuum oven, and contained 83%, 79%, 72% Reb A, respectively; 6.5%, 2.7%, 9.6% Reb D, respectively; and 0.5%, 4.0%, 0.4% Reb B, respectively.

EXAMPLE 5

Material containing ethanol crystalline form is of 93.4% Reb A, 2.4% Reb D, and 1.5% Reb B was mixed with 190-proof ethanol to produce a slurry containing 10% solids. The slurry was agitated at room temperature. After one hour, a sample of the material was filtered, washed with 190-proof ethanol, and dried. The sample contained 96% Reb A, 1.5% Reb D, and 1.6% Reb B. 89% of the glycoside material in the sample was recovered as a solid phase. The remaining slurry was held overnight, then filtered, washed with 190-proof ethanol, and dried. After an additional ~24 hours in the slurry, the crystalline product from the remaining slurry contained 96% Reb A, 1.4% Reb D, and 1.4% Reb B, and 89% of the glycoside material of the remaining slurry was recovered as a solid phase. The filtrate was collected and dried in a vacuum oven, and contained 83% Reb A, 10.4% Reb D, and 4.9% Reb B.

EXAMPLE 6

Material containing ethanol crystalline forms of 93.4% Reb A, 2.4% Reb D, and 1.5% Reb B was mixed with 190-proof ethanol to produce a slurry containing 30% solids. The slurry was heated to 70° C. and agitated. After one hour, a sample was filtered at 70° C. washed with 190-proof ethanol, and dried. The sample contained 96% Reb A, 1.8% Reb D, and 1.7% Reb B. 95% of the glycoside material in the sample was recovered as a solid phase. The filtrate was collected and dried in a vacuum oven, and contained 87% Reb A, 7.0% Reb D, and 3.9% Reb B. The slurry remaining after this sampling was held overnight, then filtered, washed with 190-proof ethanol, and dried. After an additional ~24 hours in the slurry, the crystalline product of the remaining contained 98% Reb A, 1.3% Reb D, and 0.4% Reb B, and 95% of the glycoside material was recovered from the remaining slurry as a solid phase

EXAMPLE 7

Material containing ethanol crystalline forms of 93.4% Reb A, 2.4% Reb D, and 1.5% Reb B was mixed with pure ethanol to produce a slurry containing 30% solids. The slurry was heated to 70° C. and agitated. After one hour, a sample was filtered at 70° C., washed with pure ethanol, and dried. The sample contained 95% Reb A, 2.3% Reb D, and 1.5% Reb B, and 97% of the glycoside material in the sample was recovered as a solid phase. The filtrate was collected and dried in a vacuum oven, and contained 73% Reb A, 7.7% Reb D, and 17% Reb B. The remaining slurry was held overnight, then filtered at 70° C., washed with 190-proof ethanol, and dried. After an additional ~24 hours in the slurry, the crystalline product of the remaining slurry contained 96% Reb A, 2.1% Reb D, and 1.3% Reb B, and 96% of the glycoside material of the remaining slurry was recovered as a solid phase.

EXAMPLE 8

58 g of amorphous steviol glycosides were placed in 94 wt % ethanol to produce a slurry with 20% by weight steviol glycosides. The slurry was placed in a 500 ml pressure vessel at 20 psig with an agitator and a cooling loop with 58 cm$^2$ surface area. The cooling loop was a simple U-loop of stainless steel, about 40 cm in total length, slightly offset from the center of the vessel to accommodate an agitator. The vessel was purged with nitrogen. The slurry was then heated to a bulk temperature of 100° C. over 1 hour and held at 100° C. for 2 hours. Water at 15° C. was fed to the cooling loop at 60 ml/min. The cooling water exited the cooling loop at 25° C. The pressure vessel was agitated at 180 rpm. After the two hour hold at 100°, the mixture was cooled to 70° C. over 30 minutes, filtered in a Buchner funnel at 70° C., and washed with 57 g of pure ethanol in the Buchner funnel. The solids were collected, dried, and analyzed by HPLC. 12 g of material was produced.

| | Sample Name | | | | | | | |
|---|---|---|---|---|---|---|---|---|
| | Reb D | Reb A | Stev. | Reb F | Reb C | Dulc. A | Rub. | Reb B |
| wt % glycosides of Feed Material by HPLC | 1.1 | 35.0 | 39.5 | 1.2 | 7.9 | 0.4 | 3.4 | 0.1 |
| wt % glycosides of solids by HPLC | 0.2 | 91.3 | 0.5 | 1.1 | 5.1 | 0.2 | — | 0.1 |

EXAMPLE 9

91 g of amorphous steviol glycosides were placed in 100% ethanol to produce a slurry with 30% by weight steviol glycosides. The slurry was placed in a pressure vessel according to Example 8 at 20 psig. The vessel was purged with nitrogen, then the mixture was heated to a bulk temperature of 100° C. over 1 hour and held at 100° C. for 2 hours, with flow of 60 ml/min of water at 15° C. inlet through the cooling loop with agitation of 180 rpm. The outlet temp of the cooling water was 25° C. The mixture was then cooled to 70° C. over 30 minutes, filtered at 70° C. in a Buchner funnel, and washed with 63 g of pure ethanol in the Buchner funnel. The solids were dried, and analyzed by HPLC. 8 g of material was produced.

| | Sample Name | | | | | | | | |
|---|---|---|---|---|---|---|---|---|---|
| | Reb D | Reb A | Stev. | Reb F | Reb C | Dulc. A | Rub. | Reb B | StevB |
| wt % glycosides of Feed Material by HPLC | 2.4 | 22.3 | 19.2 | 0.9 | 4.9 | 0.6 | 2.3 | 13.7 | 5.7 |
| wt % glycosides of solids by HPLC | 0.14 | 83.14 | 0.26 | 1.08 | 5.05 | 0.38 | — | 3.26 | 0.19 |

EXAMPLE 10

59 g of ethanol crystalline form Steviol glycosides were placed in 94 wt % ethanol to produce a slurry with 19% by weight steviol glycosides. The slurry was placed in a pressure vessel according to Example 8 at 20 psig. The vessel was purged with nitrogen. The slurry was then heated to a bulk temperature of 100° C. over 1 hour and held at 100° C. for 6 hours with a flow of 60 ml/min of water at 15° C. inlet through the cooling loop with agitation at 180 rpm. The outlet temp of the cooling water was 25°. The mixture was then cooled to 70° C. over 30 minutes, filtered at 70° C. and washed with 107 g of pure ethanol. The solids were collected, dried, and analyzed by HPLC. 37 g of material was recovered as product. The filtrate was collected, dried in a vacuum oven, and analyzed by HPLC.

| | Sample Name | | | | | | | | |
|---|---|---|---|---|---|---|---|---|---|
| | Reb D | Reb A | Stev. | Reb F | Reb C | Dulc. A | Rub. | Reb B | StevB |
| wt % glycosides of Feed Material by HPLC | 2.8 | 94.7 | 0.1 | 0.2 | 0.0 | — | — | 0.8 | — |
| wt % glycosides of solids by HPLC | 1.7 | 96.9 | — | 0.1 | — | — | — | 0.6 | — |
| wt % glycosides of filtrate by HPLC | 8.0 | 86.4 | 0.7 | 0.3 | 0.1 | — | — | 3.7 | — |

EXAMPLE 11

59 g of amorphous Steviol glycosides were placed in 94 wt % ethanol to produce a slurry with 19% by weight steviol glycosides. The slurry was placed in a pressure vessel according to Example 8 at 20 psig. The vessel was purged with nitrogen. The slurry was then heated to a bulk temperature of 100° C. over 1 hour and held at 100° C. for 2 hours with a flow of 60 ml/min of water at 15° C. inlet through the cooling loop and agitation at 180 rpm. The outlet temp of the cooling water was 25° C. The mixture was then cooled to 70° C. over 30 minutes, filtered at 70° C., and washed with 133 g of pure ethanol in a Buchner funnel. The solids were collected and analyzed by HPLC. 35 g of material was produced. The filtrate was collected, dried in a vacuum oven, and analyzed by HPLC.

| | Sample Name | | | | | | | | |
|---|---|---|---|---|---|---|---|---|---|
| | Reb D | Reb A | Stev. | Reb F | Reb C | Dulc. A | Rub. | Reb B | StevB |
| wt % glycosides of Feed Material by HPLC | 2.3 | 81.6 | 7.1 | 0.6 | 2.3 | 0.1 | — | 2.1 | 0.2 |
| wt % glycosides of solids by HPLC | 1.7 | 92.6 | 1.5 | 1.2 | 0.4 | — | — | 1.0 | — |
| wt % glycosides of solids by HPLC | 3.4 | 42.6 | 30.6 | 1.1 | 5.1 | 1.0 | — | 8.3 | 2.7 |

EXAMPLE 12

60 g of amorphous Steviol glycosides were placed in pure ethanol to produce a slurry with 19% by weight steviol glycosides. The slurry was placed in a pressure vessel according to Example 8 at 20 psig. The vessel was purged with nitrogen. The slurry was then heated to a bulk temperature of 100° C. over 1 hour and held at 100° C. for 2 hours with agitation at 180 rpm and with flow of 60 ml/min of water at 15° C. inlet through the cooling loop. The outlet temp of the cooling water was 25° C. The mixture was then cooled to 70° C., filtered at 70° C., and washed with 148 g of pure ethanol. The solids were collected and analyzed by HPLC. 46 g of material was produced. The filtrate was collected, dried in a vacuum oven, and analyzed by HPLC.

| | Sample Name | | | | | | | | |
|---|---|---|---|---|---|---|---|---|---|
| | Reb D | Reb A | Stev. | Reb F | Reb C | Dulc. A | Rub. | Reb B | StevB |
| wt % glycosides of Feed Material by HPLC | 2.3 | 81.6 | 7.1 | 0.6 | 2.3 | 0.1 | — | 2.1 | 0.2 |
| wt % glycosides of solids by HPLC | 2.2 | 88.3 | 3.5 | 0.5 | 1.7 | — | — | 1.5 | — |
| wt % glycosides of filtrate by HPLC | 4.9 | 24.3 | 38.4 | 1.1 | 5.9 | 1.7 | — | 8.4 | 2.7 |

EXAMPLE 13

Example without Cooling 86 g of alcohol crystalline Steviol glycosides were placed in 190-proof ethanol to produce a slurry with 19% by weight steviol glycosides. The slurry was placed in a pressure vessel according to Example 8 at 20 psig. The vessel was purged with nitrogen. The slurry was then heated to 100° C. over 1 hour and held at 100° C. for 2 hours without cooling water flowing through the cooling loop. The vessel was agitated at 180 rpm. The mixture was then cooled to 70° C., filtered at 70° C., and washed with 216 g of pure ethanol. The solids were collected and analyzed by HPLC. 75 g of material was produced. The filtrate was collected and dried and analyzed by HPLC.

| | Sample Name | | | | | | | | |
|---|---|---|---|---|---|---|---|---|---|
| | Reb D | Reb A | Stev. | Reb F | Reb C | Dulc. A | Rub. | Reb B | StevB |
| wt % glycosides of Feed Material by HPLC | 1.9 | 95.8 | — | 0.1 | 0.1 | — | — | 0.9 | — |
| wt % glycosides of solids by HPLC | 1.5 | 97.1 | — | 0.1 | — | — | — | 0.4 | — |
| wt % glycosides of filtrate by HPLC | 6.4 | 63.8 | 1.7 | 0.8 | — | 0.1 | — | 18.8 | — |

EXAMPLE 14

Example with Cooling 86 g of alcohol crystalline Steviol glycosides were placed in 190-proof ethanol to produce a slurry with 19% by weight steviol glycosides. The slurry was placed in a pressure vessel according to Example 8 at 20 psig. The vessel was purged with nitrogen. The slurry was then heated to 100° C. over 1 hour and held at 100° C. for two hours with flow of 60 ml/min of water at 15° C. inlet through the cooling loop. The outlet temp of the cooling water was 25° C. The vessel was agitated at 180 rpm. The mixture was then cooled to 70° C., filtered at 70° C., and washed with 216 g of pure ethanol. The solids were collected and analyzed by HPLC. 75 g of material was produced. The filtrate was collected and dried and analyzed by HPLC.

| | Sample Name | | | | | | | | |
|---|---|---|---|---|---|---|---|---|---|
| | Reb D | Reb A | Stev. | Reb F | Reb C | Dulc. A | Rub. | Reb B | StevB |
| wt % glycosides of Feed Material by HPLC | 1.9 | 95.8 | — | 0.1 | 0.1 | — | — | 0.9 | — |
| wt % glycosides of solids by HPLC | 1.0 | 97.8 | — | 0.1 | — | — | — | 0.3 | — |
| wt % glycosides of filtrate by HPLC | 7.2 | 67.4 | 1.3 | 0.9 | 0.2 | 0.1 | — | 15.7 | — |

Other embodiments of this invention will be apparent to those skilled in the art upon consideration of this specification or from practice of the invention disclosed herein. Various omissions, modifications, and changes to the principles and embodiments described herein may be made by one skilled in the art without departing from the true scope and spirit of the invention which is indicated by the following claims. All patents, patent documents, and publications cited herein are hereby incorporated by reference as if individually incorporated.

What is claimed is:

1. A method of treating a glycoside mixture comprising two or more of rebaudioside A material, rebaudioside B material or rebaudioside D material to help recover at least one of rebaudioside A material, rebaudioside B material or rebaudioside D material in more pure form, comprising the steps of
    a) providing a slurry comprising glycosides including at least rebaudioside A material, rebaudioside B material and rebaudioside D material, wherein the slurry includes a solid phase and a liquid phase; and
    b) aging the slurry at one or more elevated temperatures independently greater than about 85° C., said aging occurring for a time period and under conditions sufficient for at least one of (i) the solid phase to become more pure with respect to rebaudioside A material relative to at least one of rebaudioside B material and rebaudioside D material; and/or (ii) the liquid phase to become more pure with respect to at least one of rebaudioside B material and rebaudioside D material relative to rebaudioside A material.

2. The method of claim 1, further comprising the step of, after aging, recovering rebaudioside A material in the solid phase.

3. The method of claim 1, further comprising the step of, after aging, recovering at least one of rebaudioside B material and rebaudioside D material in the liquid phase and processing the liquid phase to recover a solid phase containing at least one of rebaudioside B material and rebaudioside D material.

4. The method of claim 1, wherein aging occurs at an absolute pressure greater than ambient pressure.

5. The method of claim 1, wherein aging occurs at an absolute pressure in the range from about 1.1 atm to about 5 atm.

6. The method of claim 1, wherein the slurry provided in step (a) includes less than about 60 weight percent rebaudioside A material based on the total weight of glycosides in the slurry and wherein the liquid phase comprises ethanol.

7. The method of claim 1, wherein the slurry provided in step (a) includes less than about 30 weight percent rebaudioside A material based on the total weight of glycosides in the slurry and wherein the liquid phase comprises ethanol.

8. The method of claim 1, wherein the slurry provided in step (a) includes less than about 45 weight percent rebaudioside A material and at least 10 weight percent stevioside material based on the total weight of glycosides in the slurry and wherein the liquid phase comprises ethanol.

9. The method of claim 1, wherein aging occurs with mixing in the presence of a cooling surface that is at a temperature less than the bulk temperature of the mixture.

* * * * *